(12) United States Patent
Hippensteel et al.

(10) Patent No.: US 8,608,049 B2
(45) Date of Patent: Dec. 17, 2013

(54) METHOD FOR BONDING A TANTALUM STRUCTURE TO A COBALT-ALLOY SUBSTRATE

(75) Inventors: Gregory M. Hippensteel, South Whitley, IN (US); Lawrence F. Peek, Warsaw, IN (US); Jeffrey P. Anderson, Warsaw, IN (US); Devendra Gorhe, Warsaw, IN (US); Steve M. Allen, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 832 days.

(21) Appl. No.: 11/870,205

(22) Filed: Oct. 10, 2007

(65) Prior Publication Data

US 2009/0098310 A1    Apr. 16, 2009

(51) Int. Cl.
*B23K 20/00*    (2006.01)
(52) U.S. Cl.
USPC ... 228/194; 228/193; 228/262.1; 228/262.71; 428/660; 428/613
(58) Field of Classification Search
USPC .......... 228/193, 194, 262.1, 262.71; 428/660, 428/613
See application file for complete search history.

(56) References Cited

U.S. PATENT DOCUMENTS

| | | | |
|---|---|---|---|
| 3,353,259 A | 11/1967 | Kirkpatrick | |
| 3,605,123 A | 9/1971 | Hahn | |
| 3,643,658 A | 2/1972 | Steinemenan | |
| 3,852,045 A | 12/1974 | Wheeler et al. | |
| 3,855,638 A | 12/1974 | Pilliar | |
| 4,004,064 A | 1/1977 | Kessler | |
| 4,005,988 A | 2/1977 | Paulonis et al. | |
| 4,479,271 A | 10/1984 | Bolesky et al. | |
| 4,563,489 A | 1/1986 | Urist | |
| 4,570,271 A | 2/1986 | Sump | |
| 4,673,409 A | 6/1987 | Van Kampen | |
| 4,713,076 A | 12/1987 | Draenert | |
| 4,923,471 A | 5/1990 | Morgan | |
| 5,013,324 A | 5/1991 | Zolman et al. | |
| 5,084,050 A | 1/1992 | Draenert | |
| 5,198,308 A | 3/1993 | Shetty et al. | |
| 5,282,861 A | 2/1994 | Kaplan | |
| 5,302,414 A | 4/1994 | Alkhimov | |
| 5,323,954 A | 6/1994 | Shetty et al. | |

(Continued)

FOREIGN PATENT DOCUMENTS

AU    2008229804 B2    12/2012
CH    657519    9/1986

(Continued)

OTHER PUBLICATIONS

ISR/WO From PCT/US2009/032608.

(Continued)

*Primary Examiner* — Nicholas P D'Aniello
(74) *Attorney, Agent, or Firm* — Schwegman, Lundberg & Woessner P.A.

(57) ABSTRACT

A method for bonding a porous tantalum structure to a substrate is provided. The method comprises providing a substrate comprising cobalt or a cobalt-chromium alloy; an interlayer consisting essentially of at least one of hafnium, manganese, niobium, palladium, zirconium, titanium, or alloys or combinations thereof; and a porous tantalum structure. Heat and pressure are applied to the substrate, the interlayer, and the porous tantalum structure to achieve solid-state diffusion between the substrate and the interlayer and between the interlayer and the porous tantalum structure.

19 Claims, 2 Drawing Sheets

(56) References Cited

U.S. PATENT DOCUMENTS

| | | |
|---|---|---|
| 5,363,554 A | 11/1994 | Partridge et al. |
| 5,383,934 A | 1/1995 | Armini |
| 5,397,796 A | 3/1995 | Zoller |
| 5,447,724 A | 9/1995 | Helmus |
| 5,458,653 A | 10/1995 | Davidson |
| 5,470,829 A | 11/1995 | Prisell |
| 5,492,697 A | 2/1996 | Boyan |
| 5,529,914 A | 6/1996 | Hubbell |
| 5,534,524 A | 7/1996 | Bonewald |
| 5,535,810 A | 7/1996 | Compton |
| 5,543,441 A | 8/1996 | Rhee |
| 5,550,178 A | 8/1996 | Desai |
| 5,554,594 A | 9/1996 | Zoller |
| 5,565,407 A | 10/1996 | Southard |
| 5,569,463 A | 10/1996 | Helmus |
| 5,573,934 A | 11/1996 | Hubbell |
| 5,631,011 A | 5/1997 | Wadstrom |
| 5,658,334 A | 8/1997 | Caldarise |
| 5,658,935 A | 8/1997 | Kingler |
| 5,665,118 A | 9/1997 | LaSalle |
| 5,688,855 A | 11/1997 | Stoy |
| 5,713,410 A | 2/1998 | LaSalle |
| 5,736,160 A | 4/1998 | Ringeisen |
| 5,788,979 A | 8/1998 | Alt |
| 5,801,033 A | 9/1998 | Hubbell |
| 5,824,651 A | 10/1998 | Nanci |
| 5,834,274 A | 11/1998 | Hubbell |
| 5,843,743 A | 12/1998 | Hubbell |
| 5,866,113 A | 2/1999 | Hendriks |
| 5,893,846 A | 4/1999 | Bales |
| 5,925,552 A | 7/1999 | Keogh |
| 5,928,916 A | 7/1999 | Keogh |
| 5,932,299 A | 8/1999 | Katoot |
| 5,947,893 A | 9/1999 | Agrawal |
| 6,004,943 A | 12/1999 | Shi |
| 6,099,562 A | 8/2000 | Ding |
| 6,120,536 A | 9/2000 | Ding |
| 6,121,027 A | 9/2000 | Clapper |
| 6,153,252 A | 11/2000 | Hossainy |
| 6,166,173 A | 12/2000 | Mao |
| 6,177,095 B1 | 1/2001 | Swahney |
| 6,179,817 B1 | 1/2001 | Zhong |
| 6,197,051 B1 | 3/2001 | Zhong |
| 6,238,687 B1 | 5/2001 | Mao |
| 6,254,634 B1 | 7/2001 | Anderson |
| 6,258,121 B1 | 7/2001 | Yang |
| 6,284,305 B1 | 9/2001 | Ding |
| 6,309,660 B1 | 10/2001 | Hsu |
| 6,313,119 B1 | 11/2001 | Peyman |
| 6,316,522 B1 | 11/2001 | Loomis |
| 6,322,797 B1 | 11/2001 | Mao |
| 6,368,658 B1 | 4/2002 | Schwarz |
| 6,395,023 B1 | 5/2002 | Summers |
| 6,395,029 B1 | 5/2002 | Levy |
| 6,419,806 B1 | 7/2002 | Holcomb et al. |
| 6,451,373 B1 | 9/2002 | Hossainy |
| 6,455,541 B1 | 9/2002 | Bonewald |
| 6,461,631 B1 | 10/2002 | Dunn |
| 6,486,232 B1 | 11/2002 | Wise |
| 6,492,356 B1 | 12/2002 | Peyman |
| 6,500,481 B1 | 12/2002 | Vanderlaan |
| 6,506,437 B1 | 1/2003 | Harish |
| 6,514,515 B1 | 2/2003 | Williams |
| 6,514,734 B1 | 2/2003 | Clapper |
| 6,527,938 B2 | 3/2003 | Bales et al. |
| 6,528,080 B2 | 3/2003 | Dunn |
| 6,540,746 B1 | 4/2003 | Buehler |
| 6,545,097 B2 | 4/2003 | Pinchuk |
| 6,558,734 B2 | 5/2003 | Koulik |
| 6,596,402 B2 | 7/2003 | Soerens |
| 6,600,010 B2 | 7/2003 | Mao |
| 6,620,194 B2 | 9/2003 | Ding |
| 6,632,446 B1 | 10/2003 | Hubbell |
| 6,656,517 B2 | 12/2003 | Michal |
| 6,669,980 B2 | 12/2003 | Hansen |
| 6,673,385 B1 | 1/2004 | Ding |
| 6,692,790 B2 | 2/2004 | Liu |
| 6,723,350 B2 | 4/2004 | Burrell |
| 6,730,324 B2 | 5/2004 | Troczynski |
| 6,733,768 B2 | 5/2004 | Hossainy |
| 6,743,521 B2 | 6/2004 | Hubbell |
| 6,746,685 B2 | 6/2004 | Williams |
| 6,749,639 B2 | 6/2004 | Lewallen |
| 6,833,192 B1 | 12/2004 | Caruso |
| 6,833,363 B2 | 12/2004 | Renier |
| 6,855,329 B1 | 2/2005 | Shakesheff |
| 6,866,860 B2 | 3/2005 | Nathan |
| 6,869,445 B1 | 3/2005 | Johnson |
| 6,872,799 B2 | 3/2005 | Nathan |
| 6,881,766 B2 | 4/2005 | Hain |
| 6,899,107 B2 | 5/2005 | Lewandrowski |
| 6,899,731 B2 | 5/2005 | Li |
| 6,921,811 B2 | 7/2005 | Zamora |
| 6,923,986 B2 | 8/2005 | Pathak |
| 6,923,996 B2 | 8/2005 | Epstein |
| 6,945,448 B2 | 9/2005 | Medlin et al. |
| 6,946,443 B2 | 9/2005 | Blanchat |
| 6,967,234 B2 | 11/2005 | Nathan |
| 6,969,400 B2 | 11/2005 | Rhee |
| 6,986,899 B2 | 1/2006 | Hossainy |
| 6,991,681 B2 | 1/2006 | Yoe |
| 6,991,802 B1 | 1/2006 | Ahola |
| 6,994,883 B2 | 2/2006 | Layrolle |
| 6,998,134 B2 | 2/2006 | Schmidmaier |
| 7,001,421 B2 | 2/2006 | Cheng |
| 7,008,979 B2 | 3/2006 | Schottman |
| 7,112,361 B2 | 9/2006 | Lynn |
| 7,148,209 B2 | 12/2006 | Hoemann |
| 7,157,096 B2 | 1/2007 | Zhang |
| 7,163,715 B1 | 1/2007 | Kramer |
| 7,185,695 B1 | 3/2007 | Santeler |
| 7,186,811 B2 | 3/2007 | Lindholm |
| 2002/0018798 A1 | 2/2002 | Sewing |
| 2002/0041899 A1 | 4/2002 | Chudzik |
| 2002/0082552 A1 | 6/2002 | Ding |
| 2002/0084194 A1 | 7/2002 | Redepenning |
| 2002/0087184 A1 | 7/2002 | Eder |
| 2002/0103526 A1 | 8/2002 | Steinke |
| 2002/0111590 A1 | 8/2002 | Davilia |
| 2002/0119179 A1 | 8/2002 | Rezania |
| 2002/0120333 A1 | 8/2002 | Keogh |
| 2002/0131989 A1 | 9/2002 | Brown |
| 2002/0151617 A1 | 10/2002 | Mao |
| 2002/0165608 A1 | 11/2002 | Llanos |
| 2002/0192182 A1 | 12/2002 | Massia |
| 2003/0004568 A1 | 1/2003 | Ken |
| 2003/0007991 A1 | 1/2003 | Masters |
| 2003/0083740 A1 | 5/2003 | Pathak |
| 2003/0088307 A1 | 5/2003 | Shulze |
| 2003/0099762 A1 | 5/2003 | Zhang |
| 2003/0113478 A1 | 6/2003 | Dang |
| 2003/0114937 A1 | 6/2003 | Leatherbury |
| 2003/0117579 A1 | 6/2003 | Morris |
| 2003/0118692 A1 | 6/2003 | Wang |
| 2003/0122124 A1 | 7/2003 | Nagano et al. |
| 2003/0124172 A1 | 7/2003 | Lopez |
| 2003/0124368 A1 | 7/2003 | Lynn |
| 2003/0129130 A1 | 7/2003 | Guire |
| 2003/0157030 A1 | 8/2003 | Davis |
| 2003/0185752 A1 | 10/2003 | Nathan |
| 2003/0219562 A1 | 11/2003 | Rypacek |
| 2003/0228264 A1 | 12/2003 | Nathan |
| 2003/0229393 A1 | 12/2003 | Kutryk |
| 2003/0232124 A1* | 12/2003 | Medlin et al. ............... 427/2.26 |
| 2004/0033249 A1 | 2/2004 | Sewing |
| 2004/0039441 A1 | 2/2004 | Rowland |
| 2004/0044404 A1 | 3/2004 | Stucke |
| 2004/0049265 A1 | 3/2004 | Ding |
| 2004/0051201 A1 | 3/2004 | Greenhalgh |
| 2004/0063654 A1 | 4/2004 | Davis |
| 2004/0081745 A1 | 4/2004 | Hansen |
| 2004/0086493 A1 | 5/2004 | Hubbell |
| 2004/0086543 A1 | 5/2004 | Keogh |
| 2004/0091462 A1 | 5/2004 | Lin |

(56) References Cited

U.S. PATENT DOCUMENTS

| | | |
|---|---|---|
| 2004/0091603 A1 | 5/2004 | Priewe |
| 2004/0093080 A1 | 5/2004 | Helmus |
| 2004/0106985 A1 | 6/2004 | Jang |
| 2004/0109892 A1 | 6/2004 | Shalaby |
| 2004/0117007 A1 | 6/2004 | Whitbourne |
| 2004/0120982 A1 | 6/2004 | Diana |
| 2004/0126405 A1 | 7/2004 | Sahatjian |
| 2004/0133271 A1 | 7/2004 | Jang |
| 2004/0137066 A1 | 7/2004 | Jayaraman |
| 2004/0138695 A1 | 7/2004 | Li |
| 2004/0147999 A1 | 7/2004 | Udipi |
| 2004/0157073 A1 | 8/2004 | Burrell |
| 2004/0170752 A1 | 9/2004 | Luthra |
| 2004/0172121 A1 | 9/2004 | Eidenschink |
| 2004/0185086 A1 | 9/2004 | Massia |
| 2004/0215313 A1 | 10/2004 | Cheng |
| 2004/0215336 A1 | 10/2004 | Udipi |
| 2004/0241202 A1 | 12/2004 | Chluba |
| 2004/0241234 A1 | 12/2004 | Vilkov |
| 2005/0025752 A1 | 2/2005 | Kutryk |
| 2005/0025799 A1 | 2/2005 | Hossainy |
| 2005/0031689 A1 | 2/2005 | Shults |
| 2005/0031793 A1 | 2/2005 | Moeller |
| 2005/0036946 A1 | 2/2005 | Pathak |
| 2005/0048121 A1 | 3/2005 | East |
| 2005/0049694 A1 | 3/2005 | Neary |
| 2005/0060028 A1 | 3/2005 | Horres |
| 2005/0079200 A1 | 4/2005 | Rathenow |
| 2005/0084515 A1 | 4/2005 | Udipi |
| 2005/0085605 A1 | 4/2005 | Nathan |
| 2005/0095267 A1 | 5/2005 | Campbell |
| 2005/0101692 A1 | 5/2005 | Sohier |
| 2005/0106204 A1 | 5/2005 | Hossainy |
| 2005/0112170 A1 | 5/2005 | Hossainy |
| 2005/0112172 A1 | 5/2005 | Pacetti |
| 2005/0129731 A1 | 6/2005 | Horres |
| 2005/0147647 A1 | 7/2005 | Glauser |
| 2005/0149171 A1 | 7/2005 | McCullagh et al. |
| 2005/0152955 A1 | 7/2005 | Akhave |
| 2005/0153429 A1 | 7/2005 | Liebmann-Vinson |
| 2005/0154442 A1 | 7/2005 | Eidenschink |
| 2005/0154450 A1 | 7/2005 | Larson |
| 2005/0158359 A1 | 7/2005 | Epstein |
| 2005/0165128 A1 | 7/2005 | Cohn |
| 2005/0169882 A1 | 8/2005 | Lowe |
| 2005/0169969 A1 | 8/2005 | Li |
| 2005/0180919 A1 | 8/2005 | Tedeschi |
| 2005/0183259 A1 | 8/2005 | Eidenschink |
| 2005/0187376 A1 | 8/2005 | Pacetti |
| 2005/0187602 A1 | 8/2005 | Eidenschink |
| 2005/0187611 A1 | 8/2005 | Ding |
| 2005/0191333 A1 | 9/2005 | Hsu |
| 2005/0208093 A1 | 9/2005 | Glauser |
| 2005/0208100 A1 | 9/2005 | Weber |
| 2005/0208200 A1 | 9/2005 | Ding |
| 2005/0214339 A1 | 9/2005 | Tang |
| 2005/0215722 A1 | 9/2005 | Pinchunk |
| 2005/0220837 A1 | 10/2005 | Disegi |
| 2005/0220839 A1 | 10/2005 | DeWitt |
| 2005/0220840 A1 | 10/2005 | DeWitt |
| 2005/0220841 A1 | 10/2005 | DeWitt |
| 2005/0220842 A1 | 10/2005 | DeWitt |
| 2005/0220843 A1 | 10/2005 | DeWitt |
| 2005/0244453 A1 | 11/2005 | Stucke |
| 2005/0244459 A1 | 11/2005 | DeWitt |
| 2005/0244636 A1 | 11/2005 | Ding |
| 2005/0245637 A1 | 11/2005 | Hossainy |
| 2005/0251250 A1 | 11/2005 | Verhoeven |
| 2005/0255142 A1 | 11/2005 | Chudzik |
| 2005/0266038 A1 | 12/2005 | Glauser |
| 2005/0266077 A1 | 12/2005 | Royer |
| 2005/0271700 A1 | 12/2005 | DesNoyer |
| 2005/0271701 A1 | 12/2005 | Cottone |
| 2005/0274478 A1 | 12/2005 | Verner |
| 2005/0283224 A1 | 12/2005 | King |
| 2005/0288229 A1 | 12/2005 | Sindrey |
| 2006/0003008 A1 | 1/2006 | Gibson |
| 2006/0008500 A1 | 1/2006 | Chavan |
| 2006/0009839 A1 | 1/2006 | Tan |
| 2006/0013850 A1 | 1/2006 | Domb |
| 2006/0018948 A1 | 1/2006 | Guire |
| 2006/0025848 A1 | 2/2006 | Weber |
| 2006/0035854 A1 | 2/2006 | Goldstein |
| 2006/0036311 A1 | 2/2006 | Nakayama |
| 2006/0036316 A1 | 2/2006 | Zeltinger |
| 2006/0039947 A1 | 2/2006 | Schmidmaier |
| 2006/0039950 A1 | 2/2006 | Zhou |
| 2006/0045901 A1 | 3/2006 | Weber |
| 2006/0057277 A1 | 3/2006 | Chappa |
| 2006/0067969 A1 | 3/2006 | Lu |
| 2006/0093646 A1 | 5/2006 | Cima |
| 2006/0105018 A1 | 5/2006 | Epstein |
| 2006/0121081 A1 | 6/2006 | Labrecque |
| 2006/0165754 A1 | 7/2006 | Ranade |
| 2006/0188541 A1 | 8/2006 | Richelsoph |
| 2006/0198868 A1 | 9/2006 | DeWitt |
| 2006/0204536 A1 | 9/2006 | Shults |
| 2006/0204542 A1 | 9/2006 | Zhang |
| 2006/0210598 A1 | 9/2006 | Evans |
| 2006/0210602 A1 | 9/2006 | Sehl |
| 2006/0216772 A1 | 9/2006 | Grinstaff |
| 2006/0222681 A1 | 10/2006 | Richard |
| 2006/0222756 A1 | 10/2006 | Davila |
| 2006/0233801 A1 | 10/2006 | Brunkow |
| 2006/0233841 A1 | 10/2006 | Brodbeck |
| 2006/0233941 A1 | 10/2006 | Olson |
| 2006/0240063 A9 | 10/2006 | Hunter et al. |
| 2006/0246103 A1 | 11/2006 | Ralph |
| 2006/0246105 A1 | 11/2006 | Molz |
| 2006/0246110 A1 | 11/2006 | Brandon |
| 2006/0247793 A1 | 11/2006 | Trieu |
| 2006/0251824 A1 | 11/2006 | Boulais |
| 2006/0252981 A1 | 11/2006 | Matsuda |
| 2006/0257377 A1 | 11/2006 | Atala |
| 2006/0263830 A1 | 11/2006 | Grinstaff |
| 2006/0263831 A1 | 11/2006 | Grinstaff |
| 2006/0264531 A1 | 11/2006 | Zhao |
| 2006/0286064 A1 | 12/2006 | Turnell |
| 2006/0286071 A1 | 12/2006 | Epstein |
| 2006/0293406 A1 | 12/2006 | Bennett |
| 2007/0016163 A1 | 1/2007 | Santini |
| 2007/0020308 A1 | 1/2007 | Richard |
| 2007/0020469 A1 | 1/2007 | Wood |
| 2007/0026043 A1 | 2/2007 | Guan |
| 2007/0032882 A1 | 2/2007 | Lodhi |
| 2007/0037737 A1 | 2/2007 | Hoemmann |
| 2007/0038300 A1 | 2/2007 | Bao |
| 2007/0041952 A1 | 2/2007 | Guilak |
| 2007/0042017 A1 | 2/2007 | Kutryk |
| 2007/0043374 A1 | 2/2007 | Evans |
| 2007/0043433 A1 | 2/2007 | Chandrasekaran |
| 2007/0045902 A1 | 3/2007 | Brauker |
| 2007/0048291 A1 | 3/2007 | Mang |
| 2007/0048292 A1 | 3/2007 | Morita |
| 2007/0053963 A1 | 3/2007 | Hotchkiss |
| 2007/0054127 A1 | 3/2007 | Hergenrother |
| 2007/0055095 A1 | 3/2007 | Chu |
| 2007/0055367 A1 | 3/2007 | Kutryk |
| 2008/0050699 A1 | 2/2008 | Zhang et al. |

FOREIGN PATENT DOCUMENTS

| | | |
|---|---|---|
| DE | 4106971 | 3/1992 |
| EP | 0372662 | 6/1990 |
| EP | 0616814 | 3/1994 |
| EP | 0616814 A1 | 9/1994 |
| EP | 1273303 | 1/2003 |
| EP | 1144018 | 3/2004 |
| EP | 1806155 | 7/2007 |
| EP | 2047937 A2 | 4/2009 |
| FR | 2914207 A1 | 10/2008 |
| JP | 62176966 A | 8/1987 |
| JP | 62235272 A | 10/1987 |
| JP | 2002348681 A | 12/2002 |

(56) References Cited

FOREIGN PATENT DOCUMENTS

| JP | 2004041726 | A | 2/2004 |
|---|---|---|---|
| JP | 2007231420 | A | 9/2007 |
| JP | 2009090121 | A | 4/2009 |
| WO | WO9307835 | | 4/1993 |
| WO | WO-9307835 | A1 | 4/1993 |
| WO | WO9628117 | | 9/1996 |
| WO | WO9738469 | | 10/1997 |
| WO | WO9738649 | A1 | 10/1997 |
| WO | WO0139680 | | 6/2001 |
| WO | WO0182989 | | 11/2001 |
| WO | WO03077772 | | 9/2003 |
| WO | WO03077772 | A1 | 9/2003 |
| WO | WO2005120203 | | 12/2005 |
| WO | WO-2006078864 | A1 | 7/2006 |
| WO | WO2007014279 | | 2/2007 |
| WO | WO2007014279 | A2 | 2/2007 |
| WO | WO2007038559 | | 4/2007 |
| WO | WO2007053022 | | 5/2007 |
| WO | WO-2012145292 | A1 | 10/2012 |

OTHER PUBLICATIONS

Jegnathian Karthiekeyan. Cold Spray Technology, Mar. 2005, pp. 33-35, ASB Industries, Barberton, OH.
ISR/WO From PCT/US2009/031502.
ISR from Application No. 08252074.2.
Uthoff. J. Orthop. Scie., 11:118-126 (2006).
Aleksyniene. Medicinia (Kaunus), vol. 40 (9): 842-849 (2004).
Termaat. J. Bone and Joint Surg., 870A(6): 1366-1378 (2005).
Morris. J. Bone and Joint Surg., 87-A(7), 1608-1618 (2005).
Pavoor. Biomat., 27, 1527-1533 (2006).
European Search Report for EP08253300.1 dated May 31, 2011.
Australian Government IP Examiner First Report for patent application AU 2008 229804 dated Jan. 1, 2012.
"U.S. Appl. No. 13/092,169, Examiner Interview Summary mailed Apr. 30, 2012", 3 pgs.
"U.S. Appl. No. 13/092,174, Examiner Interview Summary mailed Apr. 27, 2012", 3 pgs.
"European Application Serial No. 08253300.1, European Search Report mailed May 24, 2011", 4 pgs.
"U.S. Appl. No. 13/092,169, Final Office Action mailed Mar. 21, 2012", 11 pgs.
"U.S. Appl. No. 13/092,169, Non Final Office Action mailed Sep. 22, 2011", 8 pgs.
"U.S. Appl. No. 13/092,169, Response filed Feb. 21, 2012 to Non Final Office Action mailed Sep. 22, 2011", 13 pgs.
"U.S. Appl. No. 13/092,169, Response filed Aug. 20, 2012 to Final Office Action mailed Mar. 21, 2012", 11 pgs.
"U.S. Appl. No. 13/092,174, Final Office Action mailed Mar. 20, 2012", 11 pgs.
"U.S. Appl. No. 13/092,174, Non Final Office Action mailed Jun. 26, 2013", 9 pgs.
"U.S. Appl. No. 13/092,174, Non Final Office Action mailed Sep. 19, 2011", 12 pgs.
"U.S. Appl. No. 13/092,174, Preliminary Amendment filed Apr. 22, 2011", 7 pgs.
"U.S. Appl. No. 13/092,174, Response filed Feb. 21, 2012 to Non Final Office Action mailed Sep. 19, 2011", 12 pgs.
"U.S. Appl. No. 13/092,174, Response filed Aug. 20, 2012 to Final Office Action mailed Mar. 20, 2012", 9 pgs.
"U.S. Appl. No. 13/092,174, Response filed Sep. 26, 2013 to Non Final Office Action mailed Jun. 26, 2013", 11 pgs.
"Australian Application Serial No. 2008229804, Office Action mailed Jan. 13, 2012", 5 pgs.
"Australian Application Serial No. 2008229804, Response Filed, Oct. 29, 2012", 14 pgs.
"European Application Serial No. 08253300.1, Extended European Search Report mailed May 31, 2011", 5 pgs.
"European Application Serial No. 08253300.1, Response filed Apr. 4, 2012 to Extended Search Report mailed May 31, 2011", 4 pgs.
"International Application Serial No. PCT/US2012/033898, International Search Report mailed Jul. 31, 2012", 5 pgs.
"International Application Serial No. PCT/US2012/033898, Written Opinion mailed Jul. 31, 2012", 17 pgs.
"Japanese Application Serial No. 2008-263235, Office Action mailed Mar. 26, 2013", 9 pgs.
"Japanese Application Serial No. 2008-263235, Response filed Sep. 18, 2013", 8 pgs.
Giulio, Maccauro, "An overview about biomedical applications of micron and nano size Tantalum", Recent Patents on Biotechnology, vol. 3, No. 3,, (2009), 157-165.
Karthikeyan, Jeganathan, "Cold Spray Technology, Advanced Materials & Processes", ASB Industries, (Mar. 2005), 33-35.

* cited by examiner

METHOD FOR BONDING A TANTALUM STRUCTURE TO A COBALT-ALLOY SUBSTRATE

FIELD OF THE INVENTION

This invention relates generally to orthopedic implants, and more particularly relates to a method for bonding a porous tantalum structure to cobalt or a cobalt-alloy orthopedic implant.

BACKGROUND OF THE INVENTION

Orthopedic implants are often utilized to help their recipients recover from injury or disease. To promote quick recovery, orthopedic implants are designed to cooperate with the body's natural inclination to heal itself. Some orthopedic implants are designed to foster osseointegration. As is known in the art, osseointegration is the integration of living bone within a man-made material, usually a porous structure. Cells in the recipient form new bone within the pores of the porous structure. Thus, the porous structure and the bone tissue become intermingled as the bone grows into the pores. Accordingly, orthopedic implants may include a porous surface to enhance fixation between the orthopedic implant and adjacent tissue. Of course, the faster the surrounding tissue grows into the porous surface, the sooner the patient may begin to resume normal activities. However, the manufacture of the orthopedic implants with porous structures is not without difficulty.

Orthopedic implants are usually made from various metals. One difficulty encountered during manufacturing is bonding separate components, each made of a different metal, together. For example, cobalt is a popular metal used to make orthopedic implants, and other popular metals include alloys of cobalt with other metals, such as chromium. The porous structure may be made from an entirely different metal, such as tantalum. In this case, bonding the porous metal to the orthopedic implant involves bonding tantalum to cobalt or to cobalt-chromium alloys. Bonding these two metals together has proved to be particularly problematic.

Thus, there is a need for an improved method of bonding of porous structures, specifically tantalum, to cobalt and cobalt-alloy implants such that the bond has sufficient strength while the corrosion resistance of the metals in the resulting implant are maintained.

SUMMARY OF THE INVENTION

The present invention provides a method for bonding a porous tantalum structure to a substrate. In one embodiment, the method comprises providing (i) a substrate comprising cobalt or a cobalt-chromium alloy; (ii) an interlayer consisting essentially of at least one of hafnium, manganese, niobium, palladium, zirconium, titanium, or alloys or combinations thereof; and (iii) a porous tantalum structure, and applying heat and pressure for a time sufficient to achieve solid-state diffusion between the substrate and the interlayer and solid-state diffusion between the interlayer and the porous tantalum structure.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
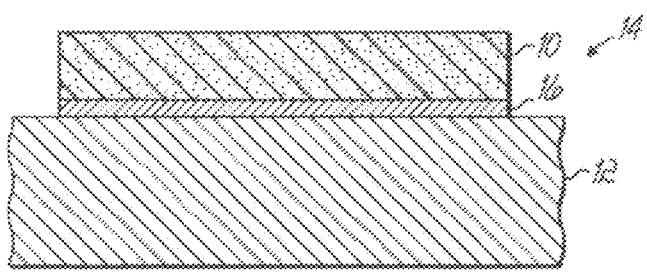
FIG. 1 depicts a cross-sectional view of one embodiment of an assembly comprising a porous tantalum structure, a preformed sheet interlayer, and a substrate.
Figure 2:
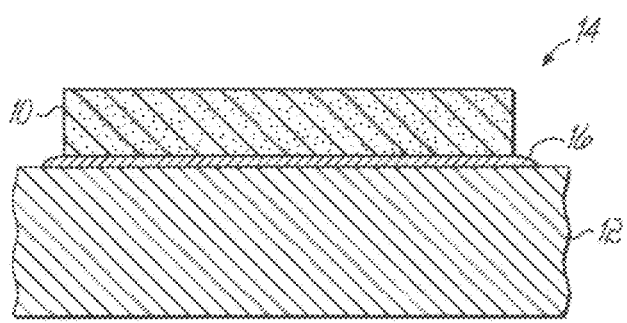
FIG. 2 depicts a cross-sectional view of another embodiment of an assembly comprising a porous tantalum structure, a coating interlayer, and a substrate.

In accordance with the present invention and with reference to FIGS. 1 and 2, a method for bonding a porous tantalum structure 10 to a substrate 12 generally begins by constructing an assembly 14 comprising an interlayer 16 placed on the surface of the substrate 12 and the porous tantalum structure 10 placed onto the interlayer 16. It will be appreciated that the assembly 14 may be constructed by placing the individual components 10, 12, 16 together in any order that results in the interlayer 16 positioned between and in contact with the substrate 12, and the porous tantalum structure 10, as shown in FIGS. 1 and 2. In other words, the placement order is not limited to those orders described herein.

The porous tantalum structure 10 may be TRABECULAR METAL®, available from Zimmer Inc., Warsaw, Ind. The porous tantalum structure 10 is configured to facilitate osseointegration. The porous tantalum structure 10 may have a pore size, pore continuity, and other features for facilitating bone tissue growth into the pores, as is known in the art.

The substrate 12 may be a cast or a wrought cobalt or cobalt chromium alloy fabricated in a shape according to the requirements for the specific orthopedic application. For example, the substrate 12 may be cast of cobalt in the shape of a total hip replacement implant. Other implants may include implants for the ankle, elbow, shoulder, knee, wrist, finger, and toe joints or other portions of the body that may benefit from a substrate 12 having a porous tantalum structure 10 bonded thereto.

With no intent to be bound by theory, tantalum and cobalt metals are not readily soluble, that is, the documented solid solubility of tantalum into cobalt is insufficient to form the necessary bond strength demanded by applications within the human body. In fact, certain stoichiometries of tantalum with cobalt may prevent solid-state diffusion of tantalum into cobalt and vice versa. Therefore, in accordance with the method of the present disclosure, the interlayer 16 comprises a metal that readily forms solid solutions with both tantalum and cobalt or cobalt-chromium alloys. For example, the interlayer 16 may be any one or an alloy of metals, such as, hafnium, manganese, niobium, palladium, zirconium, titanium, or other metals or alloys that exhibit solid solubility with tantalum at temperatures less than the melting temperature of the substrate 12, the interlayer 16, or the porous tantalum structure 10.

The assembly 14, as shown in FIGS. 1 and 2, may be put together by applying the interlayer 16 to the substrate 12. One skilled in the art will observe that the interlayer 16 may require pre-shaping to improve the contact area between the surface of the substrate 12 and the surface of interlayer 16 prior to applying the interlayer 16 to the substrate 12. Alternatively, the interlayer 16 may be press formed onto the substrate 12 such that the interlayer 16 conforms to the surface of the substrate 12. The surfaces of all components 10, 12, 16 may be cleaned prior to assembly 14 to reduce corrosion and improve solid-state diffusion bonding.

With continued reference to FIGS. 1 and 2, following application of the interlayer 16 to the substrate 12, the porous tantalum structure 10 may be placed on the interlayer 16 thus forming the assembly 14. Similar to pre-shaping the interlayer 16 to conform to the substrate 12, the porous tantalum structure 10 may be formed in a shape to maximize surface-to-surface contact to facilitate solid-state diffusion with the interlayer 16.

Heat and pressure are applied to the assembly 14 sufficient for solid-state diffusion to take place between the substrate 12 and the interlayer 16 and between the interlayer 16 and the porous tantalum structure 10. As is known to those skilled in the art, solid-state diffusion is the movement and transport of atoms in solid phases. Solid-state diffusion bonding forms a monolithic joint through formation of bonds at an atomic level due to transport of atoms between two or more metal surfaces. Heat and pressure may be supplied to the assembly 14 with a variety of methods known in the art. For example, the assembly 14 may be heated electrically, radiantly, optically, by induction, by combustion, by microwave, or other means known in the art. Pressure may be applied mechanically by clamping the assembly 14 together prior to insertion of the assembly 14 into a furnace, or pressure may be applied via a hot pressing system capable of applying pressure once the assembly 14 reaches a target temperature, as is known in the art. Furthermore, hot pressing may include hot isostatic pressing, also known in the art.

Referring now to FIG. 1, in one embodiment, the interlayer 16 is a pre-formed sheet of commercially pure titanium at least about 0.016 inches (about 0.04064 centimeter) thick. In another embodiment, the pre-formed sheet of commercially pure titanium is at least about 0.020 inches (about 0.0508 centimeter) thick for improved bond strength. It will be observed that the interlayer 16 may be positioned directly beneath the porous tantalum structure 10. In other words, it is not necessary to cover the entire substrate 12 with the interlayer 16 to bond the porous tantalum structure 10 at a single location. Furthermore, it will also be observed that the corrosion resistance and the strength of the substrate 12 are not negatively impacted if the porous tantalum structure 10 touches those areas not covered by the interlayer 16 during heating. Thus, the porous tantalum structure 10 may be bonded to multiple separate areas on the surface of the substrate 12 with multiple separate areas of interlayer 16. One skilled in the art will appreciate that the position of the porous tantalum structure 10 may be dictated by the patient's physiological requirements.

In one embodiment, the assembly 14 is clamped together by applying a pressure of at least approximately 200 pounds per square inch (psi) (approximately 1.38 MPa). However, pressures greater than approximately 200 psi may be applied up to the compressive yield strength of the any of the substrate 12, the interlayer 16, or the porous tantalum structure 10. Ordinarily, the porous tantalum structure 10 has the lowest compressive yield strength, for example, 5,800 psi for TRABECULAR METAL®.

The clamped assembly 14 is then heated to at least about 540° C. (about 1004 degree Fahrenheit) in vacuum or in another sub-atmospheric pressure of an inert atmosphere. In any case, the clamped assembly 14 is heated to less than the melting temperature of any of the components 10, 12, 16 and, in most cases, is at least about 800° C. (about 1472 degree Fahrenheit) but less than about 1000° C. (about 1832 degree Fahrenheit) in vacuum. One skilled in the art will observe that the higher the temperature, the less time it will take to achieve solid-state diffusion bonding. The time required to achieve solid-state diffusion bonding may be as little as less than 1 hour to as long as 48 hours and will depend on the metals involved, the temperatures, atmosphere, and the pressures applied.

Figure 3:
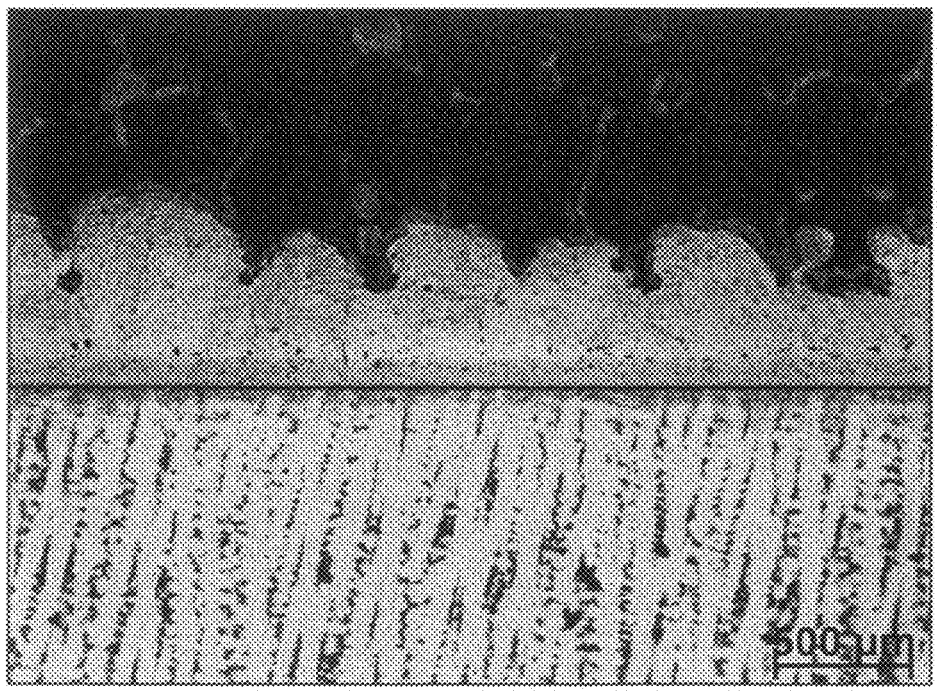
FIGS. 3 and 4 are photomicrographs corresponding to the embodiments of FIGS. 1 and 2, respectively, following heating and pressing the assembly to bond the porous tantalum structure to the interlayer and the interlayer to the substrate.

Once heated to temperature, and after a time sufficient to achieve solid-state diffusion between the porous tantalum structure 10 and the interlayer 16 and between the interlayer 16 and the substrate 12, a construct is formed. The construct may comprise the substrate 12 bonded to the interlayer 16 and the interlayer 16 bonded to the porous tantalum structure 10. FIG. 3 is a photomicrograph of a portion of the construct formed according to one embodiment of the method, described above, with a porous tantalum structure 10 (top) bonded to a titanium sheet interlayer 16 (middle) bonded to a cobalt-chromium substrate 12 (bottom).

Figure 4:
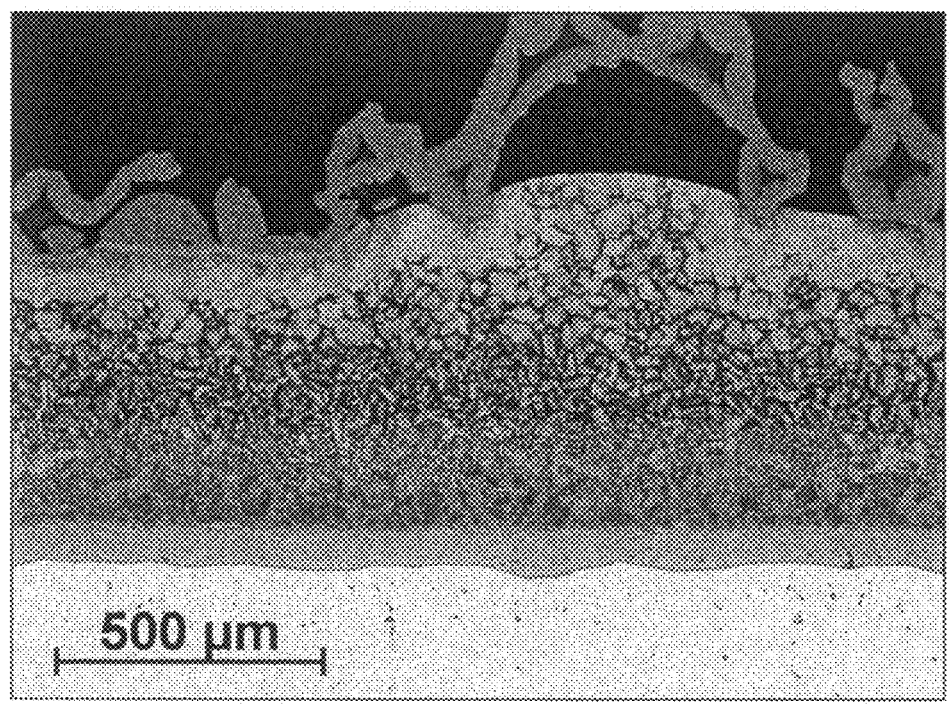

With reference now to FIG. 2, in another embodiment, the interlayer 16 is a coating applied to the surface by, for example, thermal spray, plasma spray, electron beam deposition, laser deposition, cold spray, or other method of forming the coatings on a substrate 12. In one exemplary embodiment, the coating interlayer 16 is applied via vacuum plasma spraying, as is known in the art. The substrate 12 may be masked and then grit blasted to prepare the surface of the substrate 12 for vacuum plasma spraying. In one exemplary embodiment, the substrate 12 is masked and then grit blasted with alumina (aluminum oxide) grit for increased corrosion resistance of the construct subsequent to bonding with the interlayer 16. In another exemplary embodiment, the coating interlayer 16 comprises titanium sprayed to a thickness of at least about 0.010 inches (about 0.0254 centimeter) thick. In another embodiment, for increased bond strength, the titanium coating interlayer 16 is at least about 0.020 inches (about 0.0508 centimeter) thick. In the vacuum plasma sprayed embodiments, a porosity level is between about 20% and about 40% for ease of vacuum plasma spray processing while maintaining sufficient corrosion resistance. FIG. 4 is a photomicrograph of a portion of a construct formed according to one embodiment of the method described above, showing a portion of a construct comprising a porous tantalum structure 10 (top) bonded to a titanium vacuum plasma sprayed interlayer 16 (middle) bonded to a cobalt-chromium substrate 12 (bottom).

In one exemplary embodiment, a construct comprising a porous tantalum structure 10 of TRABECULAR METAL® bonded to a titanium interlayer 16 bonded to a cobalt-chromium substrate 12 was characterized by tensile strength testing. Nearly all failure separations occurred in the porous tantalum structure 10. Tensile stresses measured at separation on constructs formed according to the previously described embodiments were routinely above 2,900 psi.

One skilled in the art will observe that heating and applying pressure may include multiple heating and pressurizing processes. For example, the porous tantalum structure 10 may be assembled with the interlayer 16 and bonded thereto, according to one embodiment of the method, to form a subassembly. That subassembly may then be bonded to the substrate 12 according to another embodiment of the method. The reverse procedure may also be used. That is, the interlayer 16 may be bonded to the substrate 12 to form a subassembly with subsequent bonding of the porous tantalum structure 10 to the interlayer portion of the subassembly. Therefore, embodiments of the method may account for different diffusion coefficients between the components 10, 12, 16 which may allow for more consistent, higher strength bonds between the substrate 12 and interlayer 16 and between the interlayer 16 and the porous tantalum structure 10. By way of further example and not limitation, diffusion bonding of a titanium interlayer 16 to a cobalt-chromium substrate 12 at an elevated temperature and pressure may take longer than diffusion bonding of the titanium interlayer 16 to a porous tantalum structure 10 at similar pressures and temperatures. Thus, by diffusion bonding the titanium interlayer 16 to the cobalt-chromium substrate 12 to form a subassembly and then diffusion bonding the porous tantalum structure 10 to the subassembly, a diffusion bond depth between the titanium interlayer 16 and the cobalt-chromium substrate 12 may be substantially the same as a diffusion bond depth between the titanium interlayer 16 and the porous tantalum structure 10. In contrast, if the porous tantalum structure 10, the titanium interlayer 16, and the cobalt-chromium substrate 12 are bonded with a single application of heat and pressure, the diffusion bond depths between the titanium interlayer 16 and the porous tantalum structure 10 and between the titanium interlayer 16 and the cobalt-chromium substrate 12 may be different.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method for bonding a porous tantalum structure to a substrate, comprising:
   providing a substrate comprising cobalt or a cobalt-chromium alloy;
   providing a preformed solid sheet consisting essentially of a metal or a metal alloy, said metal or metal alloy including at least one of hafnium, manganese, niobium, palladium, zirconium, titanium, or alloys or combinations thereof, said preformed solid sheet having a top surface and a bottom surface;
   providing a porous tantalum structure;
   applying heat and pressure to the substrate and the preformed solid sheet for a time sufficient to achieve solid-state diffusion between the substrate and the bottom surface of the preformed solid sheet; and
   applying heat and pressure to the preformed solid sheet and the porous tantalum structure for a time sufficient to achieve solid-state diffusion between the top surface of the preformed solid sheet and the porous tantalum structure, wherein the preformed solid sheet of metal defines an interlayer between the substrate and the porous tantalum structure,
   wherein said applying heat and pressure to the substrate and the preformed solid sheet and said applying heat and pressure to the preformed solid sheet and the porous tantalum structure occur concurrently.

2. The method of claim 1, wherein said preformed solid sheet is press formed onto the substrate so as to conform to the substrate prior to said applying heat and pressure to the substrate and the preformed solid sheet.

3. A method for bonding a porous tantalum structure to a substrate, comprising:
   providing a substrate comprising cobalt or a cobalt-chromium alloy;
   providing a porous tantalum structure;
   providing a preformed solid sheet having a top surface and a bottom surface, said preformed solid sheet consisting essentially of a metal or a metal alloy, said metal or metal alloy including at least one of hafnium, manganese, niobium, palladium, zirconium, titanium, or alloys or combinations thereof;
   forming an assembly which includes positioning the preformed solid sheet between the substrate and the porous tantalum structure such that the bottom surface of the preformed solid sheet contacts the substrate and the top surface of the preformed solid sheet contacts the porous tantalum structure; and
   applying heat and pressure to the assembly for a time sufficient to concurrently achieve solid-state diffusion between the substrate and the bottom surface of the preformed solid sheet and solid-state diffusion between the top surface of the preformed solid sheet and the porous tantalum structure.

4. The method of claim 3, wherein the preformed solid sheet conforms to the surface of the substrate prior to applying said heat and pressure.

5. The method of claim 3, wherein the preformed solid sheet is at least about 0.016 inches thick.

6. The method of claim 3, wherein said applying heat and pressure includes applying at least approximately 200 psi to the assembly.

7. The method of claim 3, wherein said applying heat and pressure includes applying a pressure that is less than a compressive yield strength of the porous tantalum structure.

8. The method of claim 3, wherein said applying heat and pressure includes heating to less than about 1000° C. in a vacuum environment.

9. The method of claim 3, wherein the preformed solid sheet has a thickness of at least about 0.016 inches and said applying heat and pressure includes applying a pressure of at least about 200 psi and heating the assembly to at least about 540° C. for at least one hour.

10. A method for bonding a porous tantalum structure to a substrate, comprising:
    providing a substrate comprising cobalt or a cobalt-chromium alloy;
    providing a preformed solid sheet having a top surface, a bottom surface and a thickness of at least about 0.016 inches, said preformed solid sheet consisting essentially of a metal or a metal alloy, the metal or metal alloy including at least one of hafnium, manganese, niobium, palladium, zirconium, titanium, or alloys or combinations thereof;
    providing a porous tantalum structure;
    forming an assembly which includes positioning the preformed solid sheet as an interlayer between said substrate and said porous tantalum structure, wherein the bottom surface of the preformed solid sheet contacts the substrate and the top surface of the preformed solid sheet contacts the porous tantalum structure;
    applying a pressure of at least about 200 psi to the assembly; and
    heating the assembly to at least about 540° C. for at least one hour to concurrently achieve solid-state diffusion between the substrate and the preformed solid sheet and between the preformed solid sheet and the porous tantalum structure.

11. The method of claim 1, further comprising conforming the preformed solid sheet to the substrate prior to applying said heat and pressure to the substrate and the preformed solid sheet.

12. The method of claim 1, wherein the e preformed solid sheet is pre-shaped to conform to the substrate.

13. The method of claim 1, wherein the preformed solid sheet is at least about 0.016 inches thick.

14. The method of claim 1, wherein the preformed solid sheet is at least about 0.020 inches thick.

15. The method of claim 1, wherein the preformed solid sheet is about 0.016 inches thick to about 0.020 inches thick.

16. The method of claim 3, wherein the preformed solid sheet is pre-shaped to conform to the substrate.

17. The method of claim 10, wherein said positioning includes conforming the preformed solid sheet to the substrate.

18. The method of claim 3, wherein said preformed solid sheet is press formed onto the substrate so as to conform to the substrate prior to said applying heat and pressure to the assembly.

19. The method of claim 1, wherein said applying heat and pressure to the preformed solid sheet and the porous tantalum structure includes applying a pressure that is at least 200 psi but less than the compressive yield strength of the porous tantalum structure.

* * * * *